(12) United States Patent
Lorant

(10) Patent No.: US 9,918,927 B2
(45) Date of Patent: *Mar. 20, 2018

(54) HIGH OIL CONTENT O/W EMULSIONS STABILIZED WITH A HYDROPHOBICALLY MODIFIED INULIN AND A HYDROPHILIC ACRYLIC POLYMER

(71) Applicant: L'OREAL, Paris (FR)

(72) Inventor: Raluca Lorant, Thiais (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/261,735

(22) Filed: Apr. 25, 2014

(65) Prior Publication Data

US 2014/0323431 A1 Oct. 30, 2014

Related U.S. Application Data

(63) Continuation of application No. 12/809,835, filed as application No. PCT/EP2008/067773 on Dec. 17, 2008, now Pat. No. 8,747,826.

(60) Provisional application No. 61/020,403, filed on Jan. 11, 2008, provisional application No. 61/021,046, filed on Jan. 15, 2008.

(30) Foreign Application Priority Data

| Dec. 20, 2007 | (FR) | 07 60160 |
| Dec. 20, 2007 | (FR) | 07 60162 |
| Feb. 18, 2008 | (FR) | 08 51013 |
| Feb. 18, 2008 | (FR) | 08 51018 |

(51) Int. Cl.

| A61Q 1/14 | (2006.01) |
| A61Q 17/04 | (2006.01) |
| A61Q 19/00 | (2006.01) |
| A61K 8/81 | (2006.01) |
| A61K 8/06 | (2006.01) |
| A61K 8/73 | (2006.01) |
| A61K 8/86 | (2006.01) |
| B01F 17/00 | (2006.01) |
| A61K 31/00 | (2006.01) |
| A61K 31/733 | (2006.01) |

(52) U.S. Cl.
CPC ............ *A61K 8/8158* (2013.01); *A61K 8/062* (2013.01); *A61K 8/73* (2013.01); *A61K 8/8147* (2013.01); *A61K 8/8152* (2013.01); *A61K 8/86* (2013.01); *A61K 31/00* (2013.01); *A61K 31/733* (2013.01); *A61Q 1/14* (2013.01); *A61Q 17/04* (2013.01); *A61Q 19/00* (2013.01); *A61Q 19/007* (2013.01); *B01F 17/005* (2013.01); *B01F 17/0028* (2013.01); *A61K 2800/33* (2013.01)

(58) Field of Classification Search
None
See application file for complete search history.

(56) References Cited

U.S. PATENT DOCUMENTS

| 6,759,052 | B1 | 7/2004 | Suzuki et al. |
| 8,747,826 | B2 * | 6/2014 | Lorant ............... 424/78.02 |
| 2004/0166128 | A1 | 8/2004 | Noel et al. |
| 2004/0175338 | A1 * | 9/2004 | Filippi et al. ............ 424/64 |
| 2004/0191205 | A1 | 9/2004 | Evans et al. |
| 2004/0202634 | A1 * | 10/2004 | L'Alloret ............ 424/70.16 |
| 2005/0123495 | A1 | 6/2005 | Birkel et al. |
| 2006/0172904 | A1 * | 8/2006 | Bonafos ............ A61K 8/06 510/130 |
| 2010/0331429 | A1 | 12/2010 | Lorant |

FOREIGN PATENT DOCUMENTS

| EP | 1 459 736 | 9/2004 |
| EP | 1 920 762 | 5/2008 |
| FR | 2 882 651 | 9/2006 |
| WO | 2007 017196 | 2/2007 |
| WO | WO 2007/017196 | * 2/2007 |

OTHER PUBLICATIONS

Booten, K. et al., "Polymeric, Carbohydrate-Based Surfactants and Their Use in Personal Care Applications", SOFW—Journal, vol. 130, No. 8, pp. 10-16 (Jan. 1, 2004) XP-002416632.

Noveon: "TDS-237: Neutralizing Carbopol® and Pemulen® Polymers in Aqueous and Hydroalcoholic Systems", Internet Citation, [Online], Edition: Jan. 2002, Retrieved from the Internet: URL:http://talasonline.com/photos/msds/carbopol_mixing.pdf>, pp. 1-3, [Retrieved on Aug. 8, 2008] XP-002491806.

Anonyme: "Luvigel EM: Thickener for the Production of Cosmetic Products", Internet Citation, [Online] (Jul. 1, 2000), Retrieved from the Internet: URL:http://www.creative-developments.co.uk/papers/Bathroom%20Feature%202005.pdf>, pp. 1 -10, [Retrieved on Jun. 18, 2008] XP-002484799.

* cited by examiner

*Primary Examiner* — Jyothsna A Venkat
(74) *Attorney, Agent, or Firm* — Oblon, McClelland, Maier & Neustadt, L.L.P.

(57) ABSTRACT

The invention relates to a composition in the form of an oil-in-water emulsion and its use that contains in a physiologically acceptable medium,
  i) at least 0.005% by weight, preferably at least 0.01% by weight, relative to the total weight of the composition, of at least one inulin modified with hydrophobic chains, and
  ii) at least 0.01% by weight, preferably at least 0.05% by weight, of active substance relative to the total weight of the composition, of at least one hydrophilic acrylic polymer selected from the at least partially neutralized, crosslinked acrylic homopolymers or copolymers, the polyacrylamidomethylpropanesulphonic acid (AMPS) homopolymers and mixtures thereof.

6 Claims, No Drawings

HIGH OIL CONTENT O/W EMULSIONS STABILIZED WITH A HYDROPHOBICALLY MODIFIED INULIN AND A HYDROPHILIC ACRYLIC POLYMER

This application is a continuation of U.S. application Ser. No. 12/809,835 filed on Sep. 21, 2010, now U.S. Pat. No. 8,747,826, incorporated herein by reference, which is a National Stage of PCT/EP08/067773 filed Dec. 17, 2008 and claims the benefit of U.S. 61/020,403 filed Jan. 11, 2008, U.S. 61/021,046 filed Jan. 15, 2008, FR 0760162 filed Dec. 20, 2007, FR 0760160 filed Dec. 20, 2007, FR 0851018 filed Feb. 18, 2008, and FR 0851013 filed Feb. 18, 2008.

The invention relates to the stabilization of oil-in-water emulsions containing high levels of fatty substance, even without added surfactant.

It relates to compositions in the form of oil-in-water (O/W) emulsions containing
  i) at least 0.005% by weight, preferably at least 0.01% by weight, relative to the total weight of the composition, of an inulin modified with hydrophobic chains, and
  ii) at least 0.01% by weight, preferably at least 0.05% by weight, of active substance relative to the total weight of the composition, of at least one hydrophilic acrylic polymer selected from the at least partially neutralized, crosslinked acrylic homopolymers or copolymers, the polyacrylamidomethylpropanesulphonic acid (AMPS) homopolymers and mixtures thereof.

Compositions are desired in the form of oil-in-water emulsions which are rich in fatty substances (content greater than or equal to 5% by weight, preferably greater than or equal to 10% by weight, more preferably greater than or equal to 15% by weight or even greater than or equal to 20% by weight, relative to the total weight of the composition), particularly for the care of dry skin.

However, the stabilization of these emulsions rich in fatty substances necessitates the use of emulsifying systems in combination with substantial levels of surfactants and/or thickeners, which have the drawback of making the textures sensorially heavier and of introducing a sticky, tacky feel and a certain irritant potential, particularly for persons with sensitive or reactive skin.

Conventional stabilizing systems used are, in particular, surfactant systems (sugar esters, such as sucrose laurate), fatty alcohols, alkylpolyglucosides, polyglycerol esters, and/or thickeners (xanthan gum, magnesium aluminium silicate). Moreover, in the presence of high levels of fatty substances (for example 10% by weight, relative to the total weight of the composition), it is common practice to use hydrophobic acrylic polymers (e.g. Carbopol 2020 or Pemulen) in combination with high-HLB surfactants. However, these complex systems, containing thickeners and surfactants at substantial levels, may have the drawback of making the textures sensorially heavier while at the same time introducing a sticky, tacky feel and a certain irritant potential.

The Applicant has discovered, surprisingly, that the combination (a) of a hydrophobically modified inulin which per se has poor emulsifying properties with (b) at least one particular hydrophilic acrylic polymer allows emulsions to be obtained which are stable and sensorially pleasant, in particular when the compositions contain more than 3%, or even more than 5% by weight of fatty substance, relative to the total weight of the composition, and does so even without added surfactant.

In contrast, the combination of a hydrophobically modified inulin with a hydrophobic acrylic polymer, such as a crosslinked ethoxylated (25 EO) behenyl methacrylate/AMPS copolymer, does not allow results to be obtained that are satisfactory in terms of stability and sensorial properties.

The invention provides, in particular, a composition in the form of an oil-in-water emulsion comprising, in a physiologically acceptable medium,
  i) at least 0.005% by weight, preferably at least 0.01% by weight, relative to the total weight of the composition, of an inulin modified with hydrophobic chains,
  ii) at least 0.01% by weight, preferably at least 0.05% by weight, of active substance, relative to the total weight of the composition, of at least one hydrophilic acrylic polymer selected from at least partially neutralized, crosslinked sodium polyacrylates.

This combination makes it possible in particular to obtain compounds which exhibit a particular texture which is converted, which "breaks" and which undergoes liquification on application to the skin, thereby producing an effect of freshness over the area of application.

In another embodiment the invention relates to a composition in the form of an oil-in-water emulsion comprising, in a physiologically acceptable medium,
  i) at least 0.005% by weight, preferably at least 0.01% by weight, relative to the total weight of the composition, of an inulin modified with hydrophobic chains,
  ii) at least 0.01% by weight, preferably at least 0.05% by weight, of active substance, relative to the total weight of the composition, of at least one water-superabsorbent acrylic polymer, especially crosslinked sodium polyacrylates.

This combination makes it possible in particular to obtain compositions which have an original, soft and powdery texture on application to the skin.

In particular the composition comprises at least 3% by weight, more preferably at least 5% by weight, of fatty phase, relative to the total weight of the composition. Accordingly the invention further provides a composition in the form of an oil-in-water emulsion comprising, in a physiologically acceptable medium,
  i) at least 3% by weight of a fatty phase, relative to the total weight of the composition,
  ii) at least 0.005% by weight, preferably at least 0.01% by weight, relative to the total weight of the composition, of an inulin modified with hydrophobic chains,
  iii) at least 0.01% by weight, preferably at least 0.05% by weight, of active substance, relative to the total weight of the composition, of at least one hydrophilic acrylic polymer selected from at least partially neutralized, crosslinked acrylic homopolymers or copolymers, crosslinked homopolymers of polyacrylamidomethylpropanesulphonic acid (AMPS), and mixtures thereof.

In particular the composition comprises at least 10% by weight of fatty phase, relative to the total weight of the composition.

In another embodiment the composition comprises at least 15% by weight, or even at least 20% by weight, of fatty phase, relative to the total weight of the composition.

In yet another embodiment the composition comprises at least 30% by weight of fatty phase, relative to the total weight of the composition.

The compositions according to the invention take the form of W/O emulsions, and are preferably free of emulsifying surfactants, in particular free of additional emulsifying surfactants (which would not already be introduced by the modified inulin or the hydrophilic acrylic polymer that are used according to the invention).

Compositions "free" of emulsifying surfactant are, according to the invention, compositions containing less than 1%, preferably less than 0.5%, or even less than 0.2% by weight, or 0% by weight, of emulsifying surfactant.

Hydrophobically Modified Inulin

A "hydrophobically modified inulin" according to the invention is in particular an inulin modified with hydrophobic chains, especially an inulin modified by the grafting of hydrophobic chains onto the hydrophilic backbone of said inulin.

Inulin belongs to the family of the fructans.

Fructans or fructosans are oligosaccharides or polysaccharides which comprise a sequence of anhydrofructose units optionally in combination with one or more saccharide residues other than fructose. Fructans may be linear or branched. Fructans may be products obtained directly from a plant or microbial source, or else products having a chain length which has been modified (increased or reduced) by fractionation, synthesis or hydrolysis, in particular enzymatically. Fructans generally have a degree of polymerization from 2 to approximately 1000, and preferably from 2 to approximately 60.

There are 3 distinct groups of fructans. The first group corresponds to products whose fructose units are for the most part bonded via β-2-1 bonds. These are essentially linear fructans such as inulins.

The second group also corresponds to linear fructoses, but the fructose units are essentially bonded via β-2-6 bonds. These products are levans.

The third group corresponds to mixed fructans, in other words those having β-2-6 and β-2-1 sequences. These are essentially branched fructans such as graminans.

Inulin may be obtained, for example, from endive, dahlia or Jerusalem artichoke. The inulin used in the composition according to the invention is preferably obtained, for example, from endive.

The inulins used in the compositions according to the invention are hydrophobically modified. In particular they are obtained by grafting of hydrophobic chains onto the hydrophilic backbone of the fructan.

The hydrophobic chains which can be grafted onto the main chain of the fructan may in particular be linear or branched, saturated or unsaturated hydrocarbon chains having 1 to 50 carbon atoms, such as alkyl, arylalkyl, alkylaryl and alkylene groups, divalent cycloaliphatic groups, or organopolysiloxane chains. These hydrocarbon or organopolysiloxane chains may in particular comprise one or more ester, amide, urethane, carbamate, thiocarbamate, urea, thiourea and/or sulphonamide functions, such as, in particular, methylenedicyclohexyl and isophorone, or divalent aromatic groups such as phenylene.

In particular the inulin exhibits a degree of polymerization from 2 to approximately 1000 and preferably from 2 to approximately 60, and a degree of substitution of less than 2 on the basis of one fructose unit.

According to one preferred embodiment the hydrophobic chains have at least one alkylcarbamate group of formula R—NH—CO— in which R is alkyl group having 1 to 22 carbon atoms.

According to one more-preferred embodiment the hydrophobic chains are laurylcarbamate groups.

In particular, illustrative and non-limitative instances of hydrophobically modified inulins that can be used in the compositions according to the invention include stearoyl inulin, such as those sold under the names Lifidrem INST by Engelhard and Rheopearl INS by Ciba; palmitoyl inulin; undecylenoyl inulin, such as those sold under the names Lifidrem INUK and Lifidrem INUM by Engelhard; and inulin laurylcarbamate, such as that sold under the name Inutec SP1 by Orafti.

Use is made in particular of a grafted inulin laurylcarbamate, resulting in particular from the reaction of lauryl isocyanate with an inulin, especially an inulin obtained from endive. Examples of these compounds include, in particular, the product sold under the name Inutec SP1 by Orafti.

The amount of hydrophobically modified inulin in the composition of the invention may range from 0.01% to 20% by weight, preferably from 0.01% to 10% by weight, preferably from 0.05% to 10% by weight, in particular from 0.1% to 10% by weight and preferably from 0.1% to 5% by weight, and more preferably from 0.1% to 1% by weight (of active substance) relative to the total weight of said composition.

The amount of hydrophobically modified inulin is selected as a function of the amount of fatty substance present in said composition.

Preferably, the weight ratio of hydrophobically modified inulin to fatty substance will be able to range from 1:0.1 to 0.1:60, in particular from 0.1:1 to 0.1:60, preferably from 0.1:1 to 0.1:15, more preferably from 0.1:5 to 0.1:15, and more preferably still from 0.1:8 to 0.1:12. Preferably it will be 0.1:10, in other words 0.1% of inulin for 10% of fatty substance, by weight, relative to the total weight of the composition.

By way of examples:

| % by weight of hydrophobically modified inulin relative to the total weight of the composition | % by weight of fatty substance relative to the total weight of the composition | Weight ratio (hydrophobically modified inulin/fatty substance) |
|---|---|---|
| 0.1 | 60 | 0.0017 |
| 0.1 | 40 | 0.0025 |
| 0.1 | 20 | 0.005 |
| 0.1 | 15 | 0.0067 |
| 0.1 | 12 | 0.0083 |
| 0.1 | 10 | 0.01 |
| 0.1 | 8 | 0.0125 |
| 0.1 | 5 | 0.02 |
| 1 | 0.1 | 10 |

It is equally possible to state that the weight ratio (modified inulin/fatty substance) ranges from 0.001 to 10, in particular from 0.002 to 10, preferably from 0.005 to 10, and more preferably from 0.005 to 0.02. The weight ratio (hydrophobically modified inulin/fatty substance) will preferably be less than 1, in particular less than 0.5, and more preferably still less than 0.1.

In particular it will be 0.01.

It will be possible for the hydrophobically modified inulin to be dispersed alternatively in the aqueous phase or in the oily phase, prior to emulsification. Preferably it will be dispersed in the oily phase prior to emulsification.

Hydrophilic Acrylic Polymer

The hydrophilic acrylic polymers according to the invention are, in particular, non-amphiphilic and non-hydrophobic acrylic polymers selected from the at least partially neutralized, crosslinked acrylic homopolymers or copolymers, the polyacrylamidomethylpropanesulphonic acid (AMPS) homopolymers and mixtures thereof.

The hydrophilic acrylic polymer is preferably selected from AMPS homopolymers, crosslinked sodium polyacrylates in non-particulate form, especially crosslinked acrylic polymers containing more than 90% of acrylic acid monomers, or even containing no nonionic monomer, water-superabsorbent acrylic polymers, especially crosslinked sodium polyacrylates in particulate form.

The presence of this hydrophilic acrylic polymer produces a composition which exhibits good stability properties.

The hydrophilic acrylic polymer may be present in the composition according to the invention in an amount in terms of active substance that ranges, for example, from 0.05% to 15% by weight, preferably from 0.1% to 10% by weight, more preferably from 0.1% to 6% by weight, in particular from 0.1% to 5% by weight, more preferably still from 0.1% to 4% by weight, or even from 0.1% to 3% by weight, relative to the total weight of the composition.

1/AMPS Homopolymer

The AMPS homopolymers used in the composition of the invention are advantageously water-soluble or water-dispersible or swellable in water, they may be in free form or in partially or totally neutralized form.

Preferentially the AMPS homopolymers in accordance with the invention may be partially or totally neutralized by an inorganic base (sodium hydroxide, potassium hydroxide, ammonia) or an organic base such as mono-, di- or triethanolamine, an aminomethylpropanediol, N-methylglucamine, basic amino acids such as arginine and lysine, and mixtures of these compounds. They are generally neutralized. For the purposes of the present invention, "neutralized" refers to polymers which have been totally or near-totally neutralized, in other words neutralized to an extent of at least 90%.

The AMPS homopolymers used in the composition of the invention generally have a number-average molecular weight of from 1000 to 20 000 000 g/mol, preferably from 20 000 to 5 000 000 and more preferably from 100 000 to 1 500 000 g/mol.

These polymers according to the invention may be crosslinked or non-crosslinked.

When the polymers are crosslinked, the crosslinking agents may be selected from the compounds containing olefinic polyunsaturation that are commonly used for the crosslinking of polymers obtained by free-radical polymerization.

Crosslinking agents include, for example, divinyl-benzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, the allyl ethers of alcohols from the sugars series, or other allyl or vinyl ethers of polyfunctional alcohols, and also allyl esters of derivatives of phosphoric and/or vinylphosphonic acid, or the mixtures of these compounds.

In one preferred embodiment of the invention the crosslinking agent is selected from methylenebisacrylamide, allyl methacrylate or trimethylolpropane triacrylate (TMPTA). The degree of crosslinking is in general from 0.01 to 10 mol % and more particularly from 0.2 to 2 mol %, relative to the polymer.

The homopolymer of monomers containing a sulphonic group may be crosslinked with one or more crosslinking agents.

These homopolymers are generally crosslinked and neutralized, and they may be obtained by the preparation process comprising the following steps:

(a) the monomer, such as 2-acrylamido-2-methylpropanesulphonic acid, is dispersed or dissolved in free form in a solution of tert-butanol or water and tert-butanol;
(b) the solution or dispersion of monomer obtained in (a) is neutralized with one or more organic or inorganic bases, preferably ammonia $NH_3$, in an amount producing a degree of neutralization of the sulphonic acid functions of the polymer of from 90% to 100%;
(c) the crosslinking monomer or monomers is or are added to the solution or dispersion obtained in (b);
(d) a conventional free-radical polymerization is carried out in the presence of free-radical initiators at a temperature of from 10 to 150° C., the polymer precipitating the solution or dispersion based on tert-butanol.

The preferred AMPS homopolymers are generally characterized in that they comprise, distributed at random:

a) from 90% to 99.9% by weight of units of general formula (II) below:

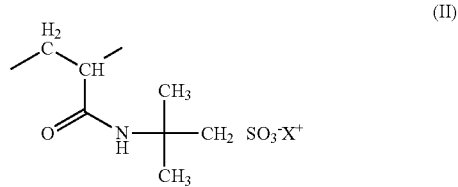

(II)

in which $X^+$ denotes a proton, an alkali metal cation, an alkaline-earth metal cation or the ammonium ion, not more than 10 mol % of the cations $X^+$ being protons $H^+$;

b) from 0.01% to 10% by weight of crosslinking units originating from at least one monomer having at least two olefinic double bonds; the proportions by weight are defined relative to the total weight of the polymer.

The homopolymers of the invention that are more particularly preferred contain from 98% to 99.5% by weight of units of formula (II) and from 0.2% to 2% by weight of crosslinking units.

Polymers of this type include in particular the crosslinked and neutralized homopolymer of 2-acrylamido-2-methylpropanesulphonic acid that is sold by Clariant under the trade name Hostacerin® AMPS (CTFA name: ammonium polyacryldimethyltauramide).

2/Crosslinked Acrylic Homopolymers or Copolymers

The crosslinked acrylic homopolymers or copolymers suitable for the invention may be present in the composition in a particulate form (water-superabsorbent polymers) or non-particulate form.

In a first embodiment the at least partially neutralized, crosslinked acrylic homopolymer or copolymer is present in the composition in a non-particulate form.

In another embodiment the at least partially neutralized, crosslinked acrylic homopolymer or copolymer is a water-superabsorbent polymer which is present in the composition in a particulate form.

2.a Neutralized and Crosslinked Acrylic Homopolymers or Copolymers in Non-Particulate Form The crosslinked acrylic polymers employed in the composition according to the invention are preferably neutralized prior to being used in the composition; that is to say, they are sold in neutralized form, in contrast to the acrylic polymers in non-neutralized form, which are neutralized in situ when the composition is formulated, by addition of a base. OK Examples of these crosslinked acrylic polymers which are already neutralized before being used, or otherwise, include:

Cosmedia SP® or crosslinked sodium polyacrylate containing 90% of dry substance and 10% of water, Cosmedia SPL® or sodium polyacrylate in inverse emulsion containing approximately 60% of dry active substance, an oil (hydrogenated polydecene) and a surfactant (PPG-5 Laureth-5), both sold by Cognis;

partially neutralized, crosslinked sodium polyacrylates which are in the form of an inverse emulsion containing at least one polar oil, an example being that sold under the name Luvigel® EM by BASF; and mixtures thereof.

A crosslinked acrylic acid polymer in accordance with the present invention that has not been neutralized beforehand may be neutralized by any appropriate means, and in particular by addition of sodium hydroxide. This gives sodium polyacrylates. Potassium polyacrylates are also suitable for the present invention.

In reality the neutralization may be carried out prior to use in the composition of the invention, if the polymer in question is sold in a non-neutralized form. In contrast, for some of these compounds, the neutralization is inherent in the primary substance. This is the case in particular with Luvigel® EM and the products called Cosmedia® SP and SPL, which are already partially neutralized.

The neutralizing step, with sodium or potassium counterions for example, is necessary in order to give the crosslinked acid polymers their property of gelling and hence of stabilizing the composition. Said crosslinked acrylic polymers are converted into corresponding acrylate polymers during this neutralizing step. The acrylic monomers of the crosslinked acrylic polymer according to the invention may be neutralized to a degree of 5% to 80%.

In one particular embodiment of the invention, the crosslinked acrylic polymer according to the invention may comprise ionic monomers. Ionic monomers which may be employed include acrylamide, methacrylamide, vinylpyrrolidone, vinylimidazole, vinylcarpolactam and hydroxyalkyl esters of carboxylic acids, such as hydroxyethyl acrylates. A particular instance of ionic monomers are unsaturated $C_3$-$C_5$ carboxylic acids. However, in the context of the present invention, preference is given to crosslinked acrylic polymers containing more than 90% of acrylic acid monomers, or even containing no nonionic monomer.

In one particular embodiment the crosslinked acrylic acid homopolymer or copolymer may be in the form of a water-in-oil emulsion, termed an inverse emulsion. This inverse emulsion may be obtained, for example, by polymerization in inverse emulsion.

In one particular embodiment of the invention, the gelling polymer employed is a partially neutralized, crosslinked sodium polyacrylate which is in the form of an inverse emulsion comprising at least one polar oil. Oils that may be mentioned include fatty acid esters. Examples of these fatty acid esters are isopropyl esters of fatty acids, such as isopropyl palmitate or isopropyl myristate, or polyglycerides of fatty acids, especially mixtures of fatty acids containing at least 50% of capric and/or caprylic acids. Water-in-oil emulsions of these kinds are described in document U.S. Pat. No. 6,197,283, which is incorporated by reference in the present application.

In this embodiment the oily phase may be composed of one or more fatty acid esters, one or more fatty acid polyglycerides based on a mixture of polyglycerides, which contains diglycerides and triglycerides, with mixtures of fatty acids, which contain caprylic acid and/or capric acid, preferably in a proportion of at least 50% by weight, relative to the total weight of fatty acids.

In one embodiment of the invention the oil content of the inverse emulsion is between 10% and 70% by weight, in particular between 15% and 35% by weight, relative to the total weight of the inverse emulsion.

On this point, mention is made in particular of Luvigel® EM, whose oily phase contains 26% of oil phase composed of $C_8$-$C_{10}$ triglycerides, namely triglycerides whose fatty acids are a mixture of capric and caprylic acids.

Furthermore, the water-in-oil emulsion may contain from 0.25% to 7% by weight, preferably 0.5% to 5% by weight, of a surfactant.

The at least partially neutralized, crosslinked acrylic polymer may be present in the inverse emulsion in an amount of from 20% to 70% by weight, in particular from 20% to 65% by weight, for example from 20% to 62% by weight, relative to the total weight of the inverse emulsion.

In particular, in one embodiment, the crosslinked acrylic polymer may be present in the inverse emulsion in an amount of from 20% to 30% by weight, relative to the total weight of the inverse emulsion. In yet another embodiment the crosslinked acrylic polymer may be present in the inverse emulsion in an amount of from 50% to 62% by weight, relative to the total weight of the composition.

The polymers in accordance with the invention may be composed of
  a) from 35% to 100% by weight of ionic monomers, the ionic monomers being 5-80% neutralized;
  b) from 0% to 65% by weight of nonionic monomers;
  c) from 0.3 to 1 mol %, relative to a) and b), of at least one at least difunctional monomer.

In the water-in-oil formulation of such a polymer, the oily phase may then be composed of one or more fatty acid esters as described above.

The acrylic acid may be crosslinked by any method known to a person skilled in the art, in particular as per the description of document U.S. Pat. No. 6,197,283 or as per the description of document U.S. Pat. No. 6,444,785, which refers to the crosslinking agents that can be used.

Among these, mention is made of the compounds containing an unsaturation that is soluble in water or in oil. Crosslinking agents of these kinds are, in particular, methylenebisacrylamide, divinylpyrrolidone, alkyl (meth)acrylate, triallylamine, ethylene glycol diacrylates (up to 50 EO), (meth)acrylic esters with dihydric or polyhydric alcohols, such as trimethylolpropane triacrylate or pentaerythritol tetraacrylate.

In one embodiment the crosslinking agent is soluble in water.

In another embodiment the crosslinking agent is triallylamine.

W/O emulsions containing a polymer in accordance with the present invention may be prepared in accordance with the teaching of document U.S. Pat. No. 6,444,785, incorporated here by reference. The objective of this process is to lower the residual monomer content by post-treatment with a redox initiator system. According to that process, the post-treatment of the W/O emulsion is carried out by adding a redox initiator system which comprises essentially
  a) 0.001% to 5% by weight, relative to the total amount of monomers used for the preparation of the polymer,
    a1) of an oxidizing agent $R^1OOH$,
  in which $R^1$ denotes hydrogen, a $C_1$ to $C_8$ alkyl group or a $C_6$ to $C_{12}$ aryl group, and/or
    a2) of a compound which releases hydrogen peroxide in aqueous medium, and b) 0.005% to 5% by weight, relative to the total amount of monomers used for the preparation of the polymer,
b1) of an α-hydroxycarbonyl compound

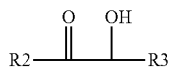

in which the groups have, independently of one another, the following meaning:
R2: hydrogen, a $C_1$-$C_{12}$ alkyl group which optionally contains functional groups and/or may contain olefinic unsaturations,
R3: hydrogen, OH, a $C_1$-$C_{12}$ alkyl group which optionally contains functional groups and/or may contain olefinic unsaturations,
and R2 and R3 may form a cyclic structure, which may contain a heteroatom and/or functional groups, and/or may contain olefinic unsaturations,
and/or
b2) of a compound which liberates an α-hydroxycarbonyl compound of this kind in aqueous medium, and
c) catalytic amounts of a multivalent metal ion which is able to exist in a plurality of valence states.

2.b Neutralized and Crosslinked, Water-Superabsorbent, Acrylic Homopolymers or Copolymers in Particulate Form In another embodiment the at least partially neutralized, crosslinked acrylic homopolymer or copolymer is present in the composition in the particulate state. The polymers in question are water-superabsorbent polymers.

A superabsorbent polymer is a polymer which swells in water, more particularly a crosslinked polymer. The superabsorbent polymer used in the composition of the invention is present in the form of particles which, when hydrated, swell to form soft beads having a number-average diameter of 10 μm to 1000 μm.

The water-superabsorbent polymer is capable in its dry state of spontaneously absorbing at least 20 times its own weight of aqueous fluid, in particular water, and especially distilled water. Superabsorbent polymers of this type are described in the work "Absorbent polymer technology, Studies in polymer science 8" by L. BRANNON-PAPPAS and R. HARLAND, Elsevier, 1990.

These polymers have a high capacity for absorption and retention of water and aqueous fluids.

By spontaneous absorption is meant an absorption time of up to 30 minutes.

The superabsorbent polymer may have a water absorption capacity of from 20 to 2000 times its own weight (i.e. 20 g to 2000 g of water absorbed per gram of absorbent polymer), preferably from 30 to 1500 times, and more preferably from 50 to 1000 times. These water absorption characteristics are defined under standard conditions of temperature (25° C.) and pressure (760 mmHg or 100 000 Pa) and for distilled water.

Mention may be made in particular of the absorbent polymers such as those sold under the names Octacare X100, X110 and RM100 by Avecia, those sold under the names Flocare GB300 and Flosorb 500 by SNF, those sold under the names Luquasorb 1003, Luquasorb 1010, Luquasorb 1280 and Luquasorb 1110 by BASF, those sold under the names Water Lock G400 and G430 (INCI name: Acrylamide/Sodium acrylate copolymer) by Grain Processing, or else AQUA KEEP 10 SH NF, which is provided by Sumitomo Seika.

The at least partially neutralized, crosslinked acrylic homopolymer or copolymer is present in the composition of the invention in an amount of active substance of, for example, from 0.03% to 15% by weight, preferably from 0.05% to 15% by weight, preferably from 0.1% to 10% by weight, more preferably from 0.1% to 7%, or even from 0.3% to 7% by weight or from 0.5% to 5% by weight, or else from 1% to 7%, and more preferably still from 2% to 5% by weight, relative to the total weight of the composition.

Generally speaking the neutralized, crosslinked acrylic homopolymers or copolymers are dispersed in the aqueous phase prior to emulsification.

In one particular embodiment said neutralized, crosslinked homopolymer or copolymer can advantageously be dispersed in the oily phase prior to emulsification. This is the case, in particular, for partially neutralized, crosslinked sodium polyacrylates which are in the form of an inverse emulsion comprising at least one polar oil, an example being that sold under the name Luvigel® EM by BASF.

Aqueous Phase

The aqueous phase generally contains water and hydrophilic adjuvants, including the monoalcohols containing 2 to 8 carbon atoms, such as ethanol and isopropanol, and the polyols such as glycerol and propanediol, the glycols such as pentylene glycol, propylene glycol, butylene glycol, isoprene glycol and the polyethylene glycols such as PEG-8; sorbitol; sugars such as glucose, fructose, maltose, lactose and sucrose; and mixtures thereof.

The water may be a floral water such as cornflower water and/or a mineral water such as water from Vittel, water from Lucas or water from La Roche Posay, and/or a thermal water.

The polyol which is miscible with water at ambient temperature (25° C.) may in particular be selected from polyols which have, in particular, 2 to 20 carbon atoms, having preferably 2 to 10 carbon atoms, and having more preferably 2 to 6 carbon atoms, such as glycerol, propylene glycol, butylene glycol, pentylene glycol, hexylene glycol, dipropylene glycol and diethylene glycol;
glycol ethers (having in particular 3 to 16 carbon atoms), such as mono-, di- or tripropylene glycol alkyl($C_1$-$C_4$) ethers, mono-, di- or triethylene glycol alkyl($C_1$-$C_4$) ethers; and mixtures thereof.

The polyol which is miscible with water at ambient temperature may be in the composition in an amount ranging from 1% to 20% by weight, relative to the total weight of the composition, and preferably ranging from 3% to 15% by weight.

The composition according to the invention may comprise a monoalcohol having 2 to 6 carbon atoms such as ethanol, isopropanol, especially in an amount ranging from 0.01% to 10% by weight, relative to the total weight of the invention, and preferably ranging from 1% to 7% by weight.

The aqueous phase (including with the polyols and other water-soluble or water-dispersible compounds) may represent from 50% to 99%, in particular from 50% to 88% by weight, 60% to 85% by weight, more preferably from 65% to 85¹% by weight, and even more preferably from 70% to 80% by weight, relative to the total weight of the composition.

Fatty (Oily) Phase

The fatty phase is present in the composition according to the invention preferably in an amount ranging from 2% to 60% by weight, more preferably from 5% to 60% by weight, relative to the total weight of the composition, preferably from 5% to 50% by weight, relative to the total weight of the composition, preferably from 8% to 40%, in particular from 10% to 40% by weight, and more preferably from 10% to 30%, or even from 15% to 30%, by weight, relative to the total weight of the composition.

In particular, the composition according to the invention comprises at least 3% by weight, preferably 5% by weight, relative to the total weight of the composition, of a fatty phase, particularly at least 3% by weight, preferably at least 5% by weight, of oils.

In one particular embodiment the composition comprises at least 10% by weight of fatty phase, in particular at least 10% of oils, relative to the total weight of the composition.

In another particular embodiment the composition comprises at least 15% by weight, or even at least 20% by weight, of fatty phase, in particular of oils, relative to the total weight of the composition.

In yet another particular embodiment the composition comprises at least 30% by weight of fatty phase, in particular at least 30% of oils, relative to the total weight of the composition.

The fatty or oily phase is composed of oils and of all of the other fatty substances and lipophilic constituents (e.g. cosmetic actives, UV filters) that may be present in the composition of the invention. Mention may be made in particular of oils, fatty esters, waxes and butters, which may be, respectively, of natural (animal, plant) or synthetic origin.

Preference will be given to using fatty substances of natural origin such as vegetable oils, fatty esters of plant origin and waxes or butters of plant origin.

According to one preferred embodiment of the invention, the oily phase contains at least one hydrocarbon oil of natural origin and/or at least one wax of natural origin.

The oily phase is a fatty phase containing at least one fatty substance selected from oils or substances which are liquid at ambient temperature (20-25° C.), and are volatile or non-volatile, and from gums and pasty fatty substances of animal, plant, mineral or synthetic origin, and mixtures thereof. These fatty substances are physiologically acceptable.

The oily phase may also comprise any common fat-soluble or fat-dispersible additive.

The oily phase preferably contains at least one oil, more particularly at least one cosmetic oil. By "oil" is meant a fatty substance which is liquid at ambient temperature (25° C.)

The oil may be a volatile oil selected in particular from volatile silicone oils and volatile non-silicone oils.

A "volatile oil" is any non-aqueous medium which is able to evaporate from the skin or lips in less than one hour, having in particular a vapour pressure at ambient temperature and atmospheric pressure which ranges from $10^{-3}$ to 300 mm Hg (0.13 Pa to 40 000 Pa).

Volatile oils which can be used in the invention may be non-silicone volatile oils, especially $C_8$-$C_{16}$ isoparaffins such as isododecane, isodecane and isohexadecane, and, for example, the oils sold under the trade names Isopar and Permethyl, and especially isododecane (Permethyl 99A).

Volatile silicone oils which can be used in the invention include the linear or cyclic silicones having to 7 silicon atoms, these silicones optionally containing alkyl or alkoxy groups having 1 to 10 carbon atoms. In particular, mention may be made of cyclohexasiloxane, cyclopentasiloxane, octamethylcyclo-tetrasiloxane, decamethylcyclopentasiloxane, dodeca-methylcyclohexasiloxane, heptamethylhexyl-trisiloxane, heptamethyloctyltrisiloxane, octamethyltrisiloxane, decamethyltetrasiloxane and mixtures thereof.

The oil may also be a non-volatile oil. A "non-volatile oil" is an oil which is capable of remaining on the skin at ambient temperature (25° C.) and atmospheric pressure for at least one hour, having more particularly a vapour pressure at ambient temperature (25° C.) and atmospheric pressure which is non-zero and is less than 0.01 mm Hg (1.33 Pa).

As a non-volatile oil which can be used in the invention, mention may be made of the following:

non-silicone, especially hydrocarbon, non-volatile oils, such as liquid paraffin (or petrolatum), squalane, hydrogenated polyisobutylene (parleam oil), perhydrosqualane, mink oil, turtle oil, soya oil, sweet almond oil, calophyllum oil, palm oil, grapeseed oil, sesame oil, corn oil, arara oil, rapeseed oil, sunflower oil, cottonseed oil, apricot oil, castor oil, avocado oil, jojoba oil, olive oil, argan oil, virgin sweet almond oil, apricot kernel oil, rice bran oil, camellia oil, or cereal germ oil; preferred oils to be used are jojoba oil, apricot kernel oil, and mixtures thereof; esters of lanolic acid, oleic acid, lauric acid and stearic acid; esters derived from long-chain alcohols or acids (i.e. those having 6 to 20 carbon atoms), especially the esters of formula RCOOR' in which R represents the residue of a higher fatty acid containing 7 to 19 carbon atoms and R' represents a hydrocarbon chain containing 3 to 20 carbon atoms, in particular the $C_{12}$-$C_{36}$ esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-occtyldodecyl myristate or lactate, di(2-ethylhexyl) succinate, diisostearyl malate, glycerol triisostearate or diglycerol triisostearate; higher fatty acids, especially $C_{14}$-$C_{22}$ acids, such as myristic acid, palmitic acid, stearic acid, behenic acid, oleic acid, linoleic acid, linolenic acid or isostearic acid; higher fatty alcohols, especially $C_{16}$-$C_{22}$ alcohols, such as cetanol, oleyl alcohol, linoleyl alcohol or linolenyl alcohol, isostearyl alcohol or octyldodecanol; and mixtures thereof.

non-volatile silicone oils such as non-volatile polydimethylsiloxanes (PDMS); polydimethylsiloxanes containing alkyl, alkoxy or phenyl groups, pendent or at the end of a silicone chain, said groups having 2 to carbon atoms; phenyl silicones such as phenyltrimethicones, phenyldimethicones, phenyl-trimethylsiloxy diphenylsiloxanes, diphenyldimethicones and diphenylmethyldiphenyltrisiloxanes; polysiloxanes modified with fatty acids (especially $C_8$-$C_{20}$ acids), fatty alcohols (especially $C_8$-$C_{20}$ alcohols) or polyoxyalkylenes (especially polyoxyethylene and/or polyoxypropylene); amino silicones; silicones containing hydroxyl groups; fluorosilicones containing a fluorine-containing group which is pendent or at the end of a silicone chain and has 1 to 12 carbon atoms, in which some or all of the hydrogens are substituted by fluorine atoms; and mixtures thereof.

The oils are selected more particularly as a function of the desired objective. Accordingly, the triglycerides and the vegetable oils such as apricot oil or olive oil are favoured for compositions intended for dry skin, whereas the fatty acid esters, which are lighter, are favoured for compositions intended for normal to mixed skin.

The other fatty substances which may be present in the oily phase are, for example, fatty acids containing 8 to 30 carbon atoms, such as stearic acid, lauric acid and palmitic acid; pasty fatty substances such as lanoline or petrolatum, waxes, such as beeswax, carnauba wax or candelilla wax, paraffin waxes, lignite waxes or microcrystalline waxes, ceresin or ozokerite, synthetic waxes such as polyethylene waxes, polymethylene waxes and Fischer-Tropsch waxes; gums such as silicone gums (dimethiconol); silicone resins such as trifluoromethyl-C1-4-alkyldimethicone and trifluoropropyldimethicone and silicone elastomers, such as the products sold under the names KSG by Shin-Etsu such as KSG 16 and KSG 6, under the name Trefil by Dow Corning or under the name Gransil by Grant Industries, and mixtures thereof.

These fatty substances may be selected variously by a person skilled in the art for the purpose of preparing a composition which has the desired properties of, for example, consistency or texture.

The amount of fatty or oily phase in the composition of the invention is greater than or equal to 5% by weight, preferably greater than or equal to 10% by weight, more preferably greater than or equal to 15%, or even greater than or equal to 20% by weight, and more preferably greater than or equal to 30% by weight, relative to the total weight of the composition.

Said amount may range, for example, from 11% to 50% by weight, preferably from 12% to 40% by weight, better still from 15% to 40% by weight, and even more preferably from 15% to 35% by weight, relative to the total weight of the composition.

In one particular embodiment the fatty phase comprises at least one lipophilic UV filter. Preferably the composition according to the invention contains at least 2% by weight, preferably at least 5% by weight, and more preferably still at least 10% by weight of at least one lipophilic UV filter, relative to the total weight of the composition.

In one particular embodiment the composition according to the invention comprises an at least partly neutralized, crosslinked acrylic homopolymer or copolymer which is present in a particulate form (for example: superabsorbent polymers) or in non-particulate form, and the fatty phase of the composition comprises at least one UV filter.

The compositions according to the invention may be cosmetic or dermatological compositions. Preferably they will be cosmetic compositions.

The composition according to the invention contains a physiologically acceptable medium.

By "physiologically acceptable medium" is meant, in the present invention, a non-toxic medium which is compatible with the skin (including the inside of the eyelids), mucous membranes, hair or lips of human beings. A cosmetic composition is a product which has a pleasant appearance, odour and feel and is intended for topical application.

Conventionally, the composition of the invention may further comprise adjuvants which are common in the fields of cosmetology and and/or dermatology, such as preservatives, antioxidants, perfumes, fillers, pigments, UV filters, odour absorbers and colorants.

According to one embodiment of the invention the composition further comprises at least one UV filter, preferably at least one lipophilic or fat-soluble UV filter.

Among the lipophilic UV filters that can be used according to the invention, mention may be made of those selected from anthranilates; cinnamic derivatives; dibenzoylmethane derivatives; salicylic derivatives; camphor derivatives; triazine derivatives, such as those described in patent applications U.S. Pat. No. 4,367,390, EP 863145, EP 517104, EP 570838, EP 796851, EP 775698, EP 878469, EP 933376, EP 507691, EP 507692, EP 790243, EP 944624; benzophenone derivatives; β,β-diphenylacrylate derivatives; benzotriazole derivatives; benzalmalonate derivatives, especially those cited in U.S. Pat. No. 5,624,663; benzimidazole derivatives; imidazolines; p-aminobenzoic acid (PABA) derivatives; benzoxazole derivatives, as described in patent applications EP 0832642, EP 1027883, EP 1300137 and DE 101 62 844; polymer filters and silicone filters, such as those described in particular in application WO 93/04665; dimers derived from α-alkylstyrene, such as those described in patent application DE 198 55 649; 4,4-diarylbutadienes such as those described in patent applications DE 197 55 649, EP 916335, EP 1133980, EP 1133981 and EP-A-1008586, and mixtures thereof.

As examples of lipophilic organic filters mention may be made of those denoted below by their INCI name:
Para-Aminobenzoic Acid Derivatives:
Ethyl PABA,
Ethyl Dihydroxypropyl PABA,
Ethylhexyl Dimethyl PABA, sold in particular under the name Escalol 507 by ISP.
Salicylic Derivatives:
Homosalate, sold under the name Eusolex HMS by Rona/EM Industries,
Ethylhexyl Salicylate, sold under the name Neo Heliopan OS by Haarmann and Reimer,
TEA Salicylate, sold under the name Neo Heliopan TS by Haarmann and Reimer.
Dibenzoylmethane Derivatives:
Butyl Methoxydibenzoylmethane, sold in particular under the trade name Parsol 1789 by Hoffmann La Roche,
Isopropyl Dibenzoylmethane.
Cinnamic Derivatives:
Ethylhexyl Methoxycinnamate, sold in particular under the trade name Parsol MCX by Hoffmann La Roche,
Isopropyl Methoxycinnamate,
Isoamyl Methoxycinnamate, sold under the trade name Neo Heliopan E 1000 by Haarmann and Reimer,
Cinoxate,
Diisopropyl Methylcinnamate.
β,β-Diphenylacrylate Derivatives:
Octocrylene, sold in particular under the trade name Uvinul N539 by BASF,
Etocrylene, sold in particular under the trade name Uvinul N35 by BASF.
Benzophenone Derivatives:
Benzophenone-1, sold under the trade name Uvinul 400 by BASF,
Benzophenone-2, sold under the trade name Uvinul D50 by BASF,
Benzophenone-3 or oxybenzone, sold under the trade name Uvinul M40 by BASF,
Benzophenone-6, sold under the trade name Helisorb 11 by Norquay,
Benzophenone-8, sold under the trade name Spectra-Sorb UV-24 by American Cyanamid,
Benzophenone-9, sold under the trade name Uvinul DS-49 by BASF,
n-hexyl 2-(4-diethylamino-2-hydroxybenzoyl)benzoate.
Benzylidene Camphor Derivatives:
3-Benzylidene camphor, manufactured under the name Mexoryl SD by Chimex,
4-Methylbenzylidene camphor, sold under the name Eusolex 6300 by Merck.
Triazine Derivatives:
Bis-Ethylhexyloxyphenol Methoxyphenyl Triazine, sold under the trade name Tinosorb S by Ciba Geigy,
Ethylhexyl triazone, sold in particular under the trade name Uvinul T150 by BASF, Diethylhexyl Butamido Triazone, sold under the trade name Uvasorb Heb by Sigma 3V,
2,4,6-tris(dineopentyl 4'-aminobenzalmalonate)-s-triazine,
2,4,6-tris(diisobutyl 4'-aminobenzalmalonate)-s-triazine.
Benzotriazole Derivatives:
Drometrizole Trisiloxane, sold under the name Silatrizole by Rhodia Chimie.
Anthranilic Derivatives:
Menthyl anthranilate, sold under the trade name Neo Heliopan MA by Haarmann and Reimer.
Imidazoline Derivatives:
Ethylhexyl Dimethoxybenzylidene Dioxoimidazoline Propionate.
Benzalmalonate Derivatives:
Dineopentyl 4'-methoxybenzalmalonate,
Polyorganosiloxanes containing benzalmalonate functions, such as Polysilicone-15, sold under the trade name Parsol SLX by Hoffmann La Roche.
4,4-Diarylbutadienes:
1,1-dicarboxy(2,2'-dimethylpropyl)-4,4-diphenyl-butadiene.
Benzoxazole Derivatives:
2,4-Bis[5-1-(dimethylpropyl)benzoxazol-2-yl-(4-phenyl)imino]-6-(2-ethylhexyl)imino-1,3,5-triazine, sold under the name Uvasorb K2A by Sigma 3V; and mixtures thereof.

The more particularly preferred lipophilic organic filters are selected from the following compounds:
Homosalate,
Ethylhexyl Salicylate,
Ethylhexyl Methoxycinnamate,
Octocrylene,
Butyl Methoxydibenzoylmethane,
Benzophenone-3,
n-hexyl 2-(4-diethylamino-2-hydroxybenzoyl)benzoate,
4-Methylbenzylidene camphor,
2,4,6-tris(dineopentyl 4'-aminobenzalmalonate)-s-triazine,
2,4,6-tris(diisobutyl 4'-aminobenzalmalonate)-s-triazine
Bis-Ethylhexyloxyphenol Methoxyphenyl Triazine,
Ethylhexyl triazone,
Diethylhexyl Butamido Triazone,
Drometrizole Trisiloxane,
Polysilicone-15,
Dineopentyl 4'-methoxybenzalmalonate,
1,1-dicarboxy(2,2'-dimethylpropyl)-4,4-diphenyl-butadiene,
2,4-bis[5-1-(dimethylpropyl)benzoxazol-2-yl-(4-phenyl)imino]-6-(2-ethylhexyl)imino-1,3,5-triazine and mixtures thereof.

And, with even more preference, from:
Homosalate,
Ethylhexyl Salicylate,
Ethylhexyl Methoxycinnamate,
Octocrylene,
Butyl Methoxydibenzoylmethane,
Ethylhexyl triazone,
Bis-Ethylhexyloxyphenol Methoxyphenyl Triazine,
Diethylhexyl Butamido Triazone,
Drometrizole Trisiloxane.

The lipophilic filters in accordance with the invention are preferably present in the compositions according to the invention in an amount ranging from 0.1% to 30% by weight and preferably from 0.5% to 15% by weight, relative to the total weight of the composition.

Preferably the composition according to the invention contains at least 2% by weight, preferably at least 5% by weight and more preferably at least 10% by weight of UV filter, relative to the total weight of the composition.

The composition according to the invention advantageously comprises at least one cosmetic or dermatological active.

Advantageously, use will be made of ingredients and/or actives that are of natural origin.

Fillers which can be used in the composition of the invention include, for example, the powders of natural organic materials such as corn, wheat or rice starches; or else materials of natural mineral origin such as silica, talc, and clays such as kaolin, montmorillonite, saponites, laponites and illites.

The amount of fillers is preferably less than or equal to 20% of the total weight of the composition, and more preferably less than or equal to 10% of the total weight of the composition, preferably less than or equal to 8%, or even less than or equal to 5%, of the total weight of the composition. When present, these fillers may be present in amounts ranging, for example, from 0.05% to 8% by weight and preferably from 0.1% to 5% by weight, relative to the total weight of the composition.

When the composition is used in the makeup sector it may include all of the fillers, dyes and pigments that are commonly used in the makeup sector.

As cosmetic or dermatological actives that can be used in the composition according to the invention, particular mention may be made of: moisturizers; free-radical scavengers; keratolytic and desquamating agents; vitamins, anti-elastase and anti-collagenase agents; trace elements; algal extracts or plankton extracts; enzymes and co-enzymes; flavonoids and isoflavonoids; ceramides; anti-glycation agents; NO-synthase inhibitors; agents which stimulate the synthesis of dermal or epidermal macromolecules and/or prevent their degradation; agents which stimulate the proliferation of fibroblasts or keratinocytes and/or the differentiation of keratinocytes; tensioning agents; anti-pollution and/or anti-radical agents; and muscle relaxants or dermal decontractants; and mixtures thereof.

Examples of actives include, for example, (N-2-hydroxyethylpiperazine-N-2-ethane)sulphonic acid (HEPES); hyaluronic acid; lanolin; urea, mixtures containing urea, such as NMF (Natural Moisturizing Factor), and urea derivatives such as N-(2-hydroxyethyl)urea (Hydrovance from National Starch); 2-oxothiazolidine-4-carboxylic acid (procysteine); α-hydroxy acids, especially fruit-derived acids, for instance glycolic acid, lactic acid, malic acid, citric acid, tartaric acid and mandelic acid, derivatives thereof and mixtures thereof; β-hydroxy acids, for instance salicylic acid and its derivatives such as 5-n-octanoylsalicylic acid or 5-n-dodecanoylsalicylic acid; α-keto acids, for instance ascorbic acid or vitamin C and its derivatives such as its salts, for instance sodium ascorbate, magnesium ascorbyl phosphate or sodium ascorbyl phosphate; its esters, for instance ascorbyl acetate, ascorbyl palmitate and ascorbyl propionate, or its sugars, for instance glycosylated ascorbic acid, and mixtures thereof; β-keto acids; retinoids such as retinol (vitamin A) and its esters, retinal, retinoic acid and its derivatives, and also the retinoids described in documents FR-A-2,570,377, EP-A-199 636, EP-A-325 540, EP-A-402 072, EP-A-325 540 and EP-A-402 072; carotenoids such as lycopene; ceramides; sapogenins and plant extracts containing them, especially extracts of wild yam; resveratrol; pseudodipeptides such as {2-[acetyl-(3-trifluoromethyl-phenyl)amino]-3-methylbutyrylamino}acetic acid; vitamins such as, for example, in addition to vitamin A and vitamin C indicated above, vitamin E (tocopherol), vitamin B3 (or vitamin PP or niacinamide), vitamin B5 (panthenol in its various forms: D-panthenol, DL-panthenol), vitamin D, vitamin F (mixture of essential fatty acids), derivatives, precursors and analogues of these vitamins; soybean extracts, in particular soybean protein hydrolysates or soybean extracts rich in isoflavones; trace elements such as copper, zinc, selenium, iron, magnesium or manganese; extracts of algae, such as the product sold under the name Stimoderm by CLR; extracts of plankton such as the plankton in aqueous dispersion (CTFA name: Vitreoscilla Ferment) sold under the name Mexoryl SAH by Chimex; enzymes; coenzymes such as ubiquinone or coenzyme Q10, which belongs to the alkylenated-chain benzoquinone family, coenzyme R, which is biotin (or vitamin H); yeast extracts such as the extract of *S. cerevisiae* sold under the name Cytovitin LS 9388 by Laboratoires Seriobiologiques; adenosine; plant extracts such as extract of licorice; calmatives such as bisabolol and calming plant extracts, for instance extracts of rose (*Rosa gallica*) and extracts of mint (*Mentha piperita*); and any active which is suitable for the ultimate purpose of the composition, and mixtures thereof.

The ingredients and/or actives will be present in the composition in amounts ranging from 0.01% to 20% by weight, preferably 0.05% to 10% and more preferably from 0.1% to 1% by weight, relative to the total weight of the composition.

These ingredients and/or actives, and their concentrations, should be such that they do not modify the property which is desired for the composition of the invention.

The composition according to the invention finds its application in a large number of treatments, especially cosmetic treatments, of the skin, including the scalp, hair, nails and/or mucous membranes, especially for the care, cleansing and/or making up and/or sun protection of the skin and/or mucous membranes.

The present invention thus further provides for the cosmetic use of the composition as defined above for the treatment, protection, care, removal of makeup from and/or cleansing of the skin, lips and/or hair, and/or for making up the skin and/or lips.

The present invention additionally provides a non-therapeutic method of caring for, making up or removing makeup from the skin, including the scalp, hair and/or lips, comprising the application to the skin, hair and/or lips of a composition as defined above.

In particular the composition according to the invention is used for the care and/or treatment of dry and/or sensitive skin.

The examples below of compositions according to the invention are given by way of illustration and without limitative character. The compounds are indicated by chemical name or by INCI name. The quantities therein are given in % by weight, unless otherwise specified.

EXAMPLES

Example 1: Comparative Examples of Stability

Moisturizing Care Cream Containing 30% Oils

| FORMULA | | Ex. a % | Ex. b % |
|---|---|---|---|
| Phase A | Preservative | qs | qs |
| | Glycerol | 3 | 3 |
| | Water | qs 100 | qs 100 |
| | Ethoxylated (25 EO) behenyl methacrylate/AMPS copolymer crosslinked with trimethylolpropane triacrylate TMPTA (Aristoflex HMB from Clariant) | 0.5 | |
| | Polyacrylamidomethylpropane-sulphonic acid, partially neutralized with ammonia and highly crosslinked (Hostacerin AMPS from Clariant) | | 0.5 |
| Phase B | Hydrophobically modified inulin (Inutec SP1 from Orafti)* | 0.3 | 0.3 |
| | Cyclohexasiloxane | 13 | 13 |
| | Isohexadecane | 7 | 7 |
| | Perhydrosqualene (from plant) | 10 | 10 |

*Inutec SP1 from Orafti at 96.5% by weight of inulin laurylcarbamate active substance.

Procedure

Preparation of phase A by dispersing the ingredients in water with stirring at 70° C. Homogenization until a smooth gel is obtained.

Emulsification at about 60° by dispersing the oily phase in the aqueous phase with stirring.

Emulsion a (comparative) containing a hydrophobic acrylic polymer has an unsatisfactory stability, as shown by its microscopic appearance from T0: a coarse emulsion is observed in which the droplet size is irregular.

Over time (2 months of storage at ambient temperature, 37° C. and 45° C.), a degradation is observed in the macroscopic appearance (more heterogeneous and shiny) and in the microscopic appearance (very coarse) of the emulsion. Moreover, there is a change in viscosity over time (thickening at T2 months at ambient temperature, and fall in viscosity at T2 months, 45° C.)

Emulsion b) according to the invention, in contrast, exhibits a microscopic appearance which is in accordance with a stable emulsion, and the stability is maintained over time under the same storage conditions.

Photoprotective Formulas

| FORMULA | | Ex. c % | Ex. d % |
|---|---|---|---|
| Phase A | Preservative | qs | qs |
| | Glycerol | 3 | 3 |
| | Water | qs 100 | qs 100 |
| | Ethoxylated (25 EO) behenyl methacrylate/AMPS copolymer crosslinked with trimethylolpropane triacrylate TMPTA (Aristoflex HMB from Clariant) | 0.5% | |
| | Polyacrylamidomethylpropane-sulphonic acid, partially neutralized with ammonia and highly crosslinked (Hostacerin AMPS from Clariant) (crosslinked AMPS homopolymer) | | 0.5 |
| Phase B | Hydrophobically modified inulin (Inutec SP1 from Orafti)* | 0.3 | 0.3 |

-continued

|   | | Ex. c % | Ex. d % |
|---|---|---|---|
| | Isononyl isononanoate | 8 | 8 |
| | Butylmethoxydibenoylmethane (Parsol 1789 from DSM Nutritional) | 3 | 3 |
| | Octocrylene | 7 | 7 |
| | Ethylhexyl salicylate | 5 | 5 |

*Inutec SP1 from Orafti at 96.5% by weight of inulin laurylcarbamate active substance.

Emulsion c (comparative, with hydrophobic acrylic polymer) is unstable: it undergoes phase separation very rapidly and, after 15 days, there is very substantial phase separation at all of the temperatures: AT, 37, 45 and 4° C.

Emulsion d (according to the invention), in contrast, is stable, and the stability is maintained under the same storage conditions.

Example 2: Formulations

Moisturizing Care Cream (30% Oils)

|   |   | % |
|---|---|---|
| Phase A | Preservative | qs |
| | Glycerol | 3 |
| | Water | qs 100 |
| | Polyacrylamidomethylpropane-sulphonic acid, partially neutralized with ammonia and highly crosslinked (Hostacerin AMPS from Clariant) | 0.5 |
| Phase B | Hydrophobically modified inulin (Inutec SP1 from Orafti)* | 0.3 |
| | Cyclohexasiloxane | 13 |
| | Isohexadecane | 7 |
| | Perhydrosqualene (from plant) | 10 |

*Inutec SP1 from Orafti at 96.5% by weight of inulin laurylcarbamate active substance.

Procedure

Preparation of phase A by dispersing the ingredients in water with stirring at 70° C. Homogenization until a smooth gel is obtained.

Emulsification at about 52° by dispersing the oily phase in the aqueous phase with stirring.

A thick cream is obtained which is transformed into a milk when applied to the skin, thus providing, from application, a calmative moisturizing and nourishing effect.

In one embodiment a moisturizing care cream is prepared which has the same composition as the previous cream, with a proportion of glycerol of 7% in place of 3% by weight, relative to the total weight of the composition.

Example 3: Comparative Examples of Stability

The inulin modified with hydrophobic chains and the hydrophilic acrylic polymer (hydrophobic in comparative example a) are dispersed in the aqueous phase.

Moisturizing Care Cream Containing 30% Oils

|   |   | Ex. a (comparative) % | Ex. b % |
|---|---|---|---|
| Phase A | Preservative | qs | qs |
| | Glycerol | 3 | 3 |
| | Water | qs 100 | qs 100 |
| | Ethoxylated (25 EO) behenyl methacrylate/AMPS copolymer crosslinked with trimethylolpropane triacrylate TMPTA (Aristoflex HMB from Clariant) - hydrophobic | 0.5% | |
| | Neutralized, crosslinked sodium polyacrylate in inverse emulsion at 26% with C8/C10 triglycerides (Luvigel EM from BASF)** | | 2 |
| Phase B | Hydrophobically modified inulin (Inutec SP1 from Orafti)* | 0.3 | 0.3 |
| | Cyclohexasiloxane | 13 | 13 |
| | Isohexadecane | 7 | 7 |
| | Perhydrosqualene (from plant) | 10 | 10 |

*Inutec SP1 from Orafti at 96.5% by weight of inulin laurylcarbamate active substance.
**Luvigel EM from BASF at 25-26% by weight of neutralized, crosslinked sodium polyacrylate active substance in inverse emulsion with C8/C10 triglycerides (2% of primary substance, corresponding to 0.5% by weight of active substance relative to the total weight of the composition).

Procedure

Preparation of phase A by dispersing the ingredients in water with stirring at 70° C. Homogenization until a smooth gel is obtained.

Emulsification at about 60° by dispersing the oily phase in the aqueous phase with stirring.

The emulsion containing a hydrophobic acrylic polymer has an unsatisfactory stability, as shown by its microscopic appearance from T0: a coarse emulsion is observed in which the droplet size is irregular.

Over time (2 months of storage at ambient temperature, 37° C. and 45° C.), a degradation is observed in the macroscopic appearance (more heterogeneous and shiny) and in the microscopic appearance (very coarse) of the emulsion. Moreover, there is a change in viscosity over time (thickening at T2 months at ambient temperature, and fall in viscosity at T2 months, 45° C.)

Emulsion b) according to the invention, in contrast, exhibits a microscopic appearance which is in accordance with a stable emulsion, and the stability is maintained over time under the same storage conditions.

Photoprotective Formulas

|   |   | Ex. c (comparative) % | Ex. d % |
|---|---|---|---|
| Phase A | Preservative | qs | qs |
| | Glycerol | 3 | 3 |
| | Water | qs 100 | qs 100 |
| | Ethoxylated (25 EO) behenyl methacrylate/AMPS copolymer crosslinked with trimethylolpropane triacrylate TMPTA (Aristoflex HMB from Clariant) | 0.5% | |
| | Neutralized, crosslinked sodium polyacrylate in inverse emulsion at 26% with C8/C10 triglycerides (Luvigel from BASF)** | | 2.5 |

-continued

|  |  | Ex. c (comparative) % | Ex. d % |
|---|---|---|---|
| Phase B | Hydrophobically modified inulin (Inutec SP1 from Orafti)* | 0.3 | 0.3 |
|  | Isononyl isononanoate | 8 | 8 |
|  | Butylmethoxydibenoylmethane (Parsol 1789) | 3 | 3 |
|  | Octocrylene | 7 | 7 |
|  | Ethylhexyl salicylate | 5 | 5 |

* Inutec SP1 from Orafti at 96.5% by weight of inulin laurylcarbamate active substance.
** Luvigel EM from BASF at 25-26% by weight of neutralized, crosslinked sodium polyacrylate active substance in inverse emulsion with C8/C10 triglycerides (2.5% of primary substance, corresponding to 0.6% by weight of active substance relative to the total weight of the composition).

Emulsion c (comparative, with hydrophobic acrylic polymer) is unstable: it undergoes phase separation very rapidly and, after 15 days, there is very substantial phase separation at all of the temperatures: AT, 37, 45 and 4° C.

Emulsion d (according to the invention), in contrast, is stable, and the stability is maintained under the same storage conditions.

Example 4: Comparative Examples of Stability

In an alternative, the inulin modified with hydrophobic chains and the hydrophilic acrylic polymer are dispersed in the oily phase.

Moisturizing Care Cream (30% Oils)

|  |  | Ex. a' (comparative) % | Ex. b' % |
|---|---|---|---|
| Phase A | Preservative | qs | qs |
|  | Glycerol | 3 | 3 |
|  | Water | qs 100 | qs 100 |
|  | Ethoxylated (25 EO) behenyl methacrylate/AMPS copolymer crosslinked with trimethylolpropane triacrylate TMPTA (Aristoflex HMB from Clariant) - hydrophobic | 0.5% |  |
| Phase B | Neutralized, crosslinked sodium polyacrylate in inverse emulsion at 26% with C8/C10 triglycerides (Luvigel from BASF)** |  | 2 |
|  | Hydrophobically modified inulin (Inutec SP1 from Orafti)* | 0.3 | 0.3 |
|  | Cyclohexasiloxane | 13 | 13 |
|  | Isohexadecane | 7 | 7 |
|  | Perhydrosqualene (from plant) | 10 | 10 |

*Inutec SP1 from Orafti at 96.5% by weight of inulin laurylcarbamate active substance.
**Luvigel EM from BASF at 25-26% by weight of neutralized, crosslinked sodium polyacrylate active substance in inverse emulsion with C8/C10 triglycerides (2% of primary substance, corresponding to 0.5% by weight of active substance relative to the total weight of the composition).

Procedure

Preparation of phase A by dispersing the ingredients in water with stirring at 70° C. Homogenization.

Emulsification at about 60° by dispersing the oily phase in the aqueous phase with stirring.

The emulsion containing a hydrophobic acrylic polymer has an unsatisfactory stability, as shown by its microscopic appearance from T0: a coarse emulsion is observed in which the droplet size is irregular.

Over time (2 months of storage at ambient temperature, 37° C. and 45° C.), a degradation is observed in the macroscopic appearance (more heterogeneous and shiny) and in the microscopic appearance (very coarse) of the emulsion. Moreover, there is a change in viscosity over time (thickening at T2 months at ambient temperature, and fall in viscosity at T2 months, 45° C.).

Emulsion b') according to the invention, in contrast, exhibits a microscopic appearance which is in accordance with a stable emulsion, and the stability is maintained over time under the same storage conditions.

Photoprotective Formulas

|  |  | Ex. c' (comparative) % | Ex. d' % |
|---|---|---|---|
| Phase A | Preservative | qs | qs |
|  | Glycerol | 3 | 3 |
|  | Water | qs 100 | qs 100 |
|  | Ethoxylated (25 EO) behenyl methacrylate/AMPS copolymer crosslinked with trimethylolpropane triacrylate TMPTA (Aristoflex HMB from Clariant) | 0.5% |  |
| Phase B | Neutralized, crosslinked sodium polyacrylate in inverse emulsion at 26% with C8/C10 triglycerides (Luvigel from BASF)** |  | 2.5 |
|  | Hydrophobically modified inulin (Inutec SP1 from Orafti)* | 0.3 | 0.3 |
|  | Isononyl isononanoate | 8 | 8 |
|  | Butylmethoxydibenzoylmethane (Parsol 1789) | 3 | 3 |
|  | Octocrylene | 7 | 7 |
|  | Ethylhexyl salicylate | 5 | 5 |

*Inutec SP1 from Orafti at 96.5% by weight of inulin laurylcarbamate active substance.
**Luvigel EM from BASF at 25-26% by weight of neutralized, crosslinked sodium polyacrylate active substance in inverse emulsion with C8/C10 triglycerides (2.5% of primary substance, corresponding to 0.6% by weight of active substance relative to the total weight of the composition).

Emulsion c' (comparative, with hydrophobic acrylic polymer) is unstable: it undergoes phase separation very rapidly and, after 15 days, there is very substantial phase separation at all of the temperatures: AT, 37, 45 and 4° C.

Emulsion d' (according to the invention), in contrast, is stable, and the stability is maintained under the same storage conditions.

Example 5: Formulation

Nourishing Moisturizing Care Cream (30% Oils)

|  |  | % |
|---|---|---|
| Phase A | Preservative | qs |
|  | Glycerol | 3 |
|  | Water | qs 100 |
|  | Neutralized, crosslinked sodium polyacrylate in inverse emulsion at 26% with C8/C10 triglycerides (Luvigel from BASF) | 2 |
| Phase B | Hydrophobically modified inulin (Inutec SP1 from Orafti)* | 0.3 |

-continued

| | % |
|---|---|
| Cyclohexasiloxane | 13 |
| Isohexadecane | 7 |
| Perhydrosqualene (from plant) | 10 |

*Inutec SP1 from Orafti at 96.5% by weight of inulin laurylcarbamate active substance.

Procedure

Preparation of phase A by dispersing the ingredients in water with stirring at 70° C. Homogenization until a smooth gel is obtained.

Emulsification at about 52° by dispersing the oily phase in the aqueous phase with stirring.

A thick cream is obtained which is transformed into a milk when applied to the skin, thus providing, from application, a calmative moisturizing effect.

In an alternative, the neutralized, crosslinked sodium polyacrylate in inverse emulsion at 26% with C8/C10 triglycerides (Luvigel from BASF) is dispersed in phase B (fatty phase) prior to emulsification.

Example 6: Moisturizing Cream

| | | % |
|---|---|---|
| Phase A | Glycerol | 5 |
| | Crosslinked polyacrylate microspheres (Aquakeep from Sumitomo Seika) | 0.4 |
| | Water | qs 100 |
| | Preservative | qs |
| Phase B | Hydrophobically modified inulin (Inutec SP1 from Orafti)* | 0.1 |
| | Dicaprylyl carbonate | 10 |

Preparation of phase A: at ambient temperature the superabsorbent polymer Aquakeep is dispersed in the glycerol and then the mixture is dispersed in the water containing the preservative.

Emulsification by dispersing the oily phase in the aqueous phase with stirring.

A cream is obtained which has a matte appearance, is fresh and melting on application, and is soft and powdery on the skin.

The invention claimed is:

1. A composition in the form of an oil-in-water emulsion comprising, in a physiologically acceptable medium,
   i) at least 0.005% by weight relative to the total weight of the composition, of an inulin modified with hydrophobic chains,
   ii) at least 0.01% by weight relative to the total weight of the composition, of a neutralized, crosslinked sodium polyacrylate, wherein the composition is stable for 2 months at 37° C. and 45° C. and which is free of surfactant.

2. The composition according to claim 1, comprising at least 15% by weight of fatty phase, relative to the total weight of the composition.

3. The composition according to claim 1, wherein the hydrophobically modified inulin/fatty substance ratio ranges from 1:0.1 to 0.1:60.

4. The composition according to claim 1, wherein the hydrophobic chains are laurylcarbamate groups.

5. The composition according to claim 1, wherein neutralized, crosslinked sodium polyacrylate is present in an amount of active substance ranging from 0.05% to 15% by weight relative to the total weight of the composition.

6. A non-therapeutic method of caring for, making up or removing makeup from the skin, including the scalp, hair and/or lips, comprising the application to the skin, hair and/or lips of a composition according to claim 1.

* * * * *